United States Patent
Inukai et al.

(10) Patent No.: US 9,063,060 B2
(45) Date of Patent: Jun. 23, 2015

(54) SOLID-STATE NMR SPECTROMETER, SAMPLE HOLDER THEREFOR, AND METHOD OF SOLID-STATE NMR SPECTROSCOPY

(75) Inventors: Munehiro Inukai, Kyoto (JP); Yasuto Noda, Kyoto (JP); Kazuyuki Takeda, Kyoto (JP); Kiyonori Takegoshi, Kyoto (JP); Takashi Mizuno, Akishima (JP)

(73) Assignees: JEOL Resonance Inc., Tokyo (JP); Kyoto University, Kyoto-shi (JP)

( * ) Notice: Subject to any disclaimer, the term of this patent is extended or adjusted under 35 U.S.C. 154(b) by 926 days.

(21) Appl. No.: 13/269,755

(22) Filed: Oct. 10, 2011

(65) Prior Publication Data

US 2013/0088232 A1    Apr. 11, 2013

(51) Int. Cl.
| | |
|---|---|
| *G01V 3/00* | (2006.01) |
| *G01N 24/08* | (2006.01) |
| *G01R 33/30* | (2006.01) |
| *G01R 33/31* | (2006.01) |
| *G01R 33/341* | (2006.01) |

(52) U.S. Cl.
CPC ............... *G01N 24/08* (2013.01); *G01R 33/30* (2013.01); *G01R 33/31* (2013.01); *G01R 33/307* (2013.01); *G01R 33/341* (2013.01)

(58) Field of Classification Search
CPC ....................................................... G01R 33/30
USPC ........................................ 324/321, 318, 322
See application file for complete search history.

(56) References Cited

U.S. PATENT DOCUMENTS

| | | | | |
|---|---|---|---|---|
| 4,254,373 | A | * | 3/1981 | Lippmaa et al. .............. 324/321 |
| 5,202,633 | A | | 4/1993 | Doty et al. |
| 5,424,644 | A | * | 6/1995 | Zeiger ........................... 324/318 |
| 2013/0088232 | A1 | * | 4/2013 | Inukai et al. ................. 324/321 |

FOREIGN PATENT DOCUMENTS

JP     62-79151 U    5/1987

OTHER PUBLICATIONS

Yasuto Noda et al., "7Li Microcoil MAS NMR Application to Cathode Materials for Thin-film Lithium Ion Batteries", (2010), p. 110, 51st ENC.

* cited by examiner

*Primary Examiner* — Louis Arana
(74) *Attorney, Agent, or Firm* — The Webb Law Firm

(57) ABSTRACT

A high-resolution solid-state NMR spectrometer which can measure a disklike sample. The spectrometer includes: a stator having an air bearing disposed within the static magnetic field, the rotor being disposed in the stator; and an engaging mechanism mounted in a one-end portion of the rotor and detachably holding a sample holder that holds the disklike sample.

10 Claims, 11 Drawing Sheets

SOLID-STATE NMR SPECTROMETER, SAMPLE HOLDER THEREFOR, AND METHOD OF SOLID-STATE NMR SPECTROSCOPY

BACKGROUND OF THE INVENTION

1. Field of the Invention

The present invention relates to a high-resolution solid-state NMR spectrometer used when nuclear magnetic resonance (NMR) spectra are acquired from disklike solid samples such as wafers. The invention also relates to a sample holder used in this spectrometer and to a method of solid-state NMR spectroscopy.

2. Description of the Related Art

An NMR spectrometer is an analytical instrument for detecting a signal arising from atomic nuclei having spin magnetic moments by applying a static magnetic field to the nuclei to induce the spin magnetic moments to produce a Larmor precession and irradiating the nuclei with RF waves having the same frequency as the precession to bring the nuclei into resonance.

Samples to be investigated by NMR include two types: solution samples and solid samples. Among them, many solution samples give quite sharp NMR spectra and, therefore, it is widespread to perform molecular structural analysis of chemical substances by making full use of the excellent performance of the obtained high-resolution NMR spectra.

On the other hand, in an NMR spectrum of a sample in solid phase, interactions (such as dipolar interactions) which would be nullified by rotational Brownian motion in a solution manifest themselves directly and so the spectral linewidth broadens extremely, thus obscuring chemical shift terms. Therefore, in an NMR spectrum, it is impossible to isolate the signal peaks arising from various portions of a molecule under investigation. As a result, it has been thought that solid-state NMR spectroscopy is unsuited for molecular structural analysis.

A method which overcomes this undesired phenomenon and gives rise to sharp solid-state NMR spectra was discovered by E. R. Andrew in 1958. In particular, anisotropic interactions are removed and chemical shift terms can be extracted by tilting the sample tube at an angle of about 54.7° to the direction of the static magnetic field $B_0$ and spinning the tube at high speed. This method is known as MAS (magic angle spinning).

A solid-state NMR instrument includes a mechanism for adjusting the angle of the axis of spinning of a sample tube. The mechanism is shown in the block diagram of FIG. 1. The instrument has a probe, generally indicated by reference numeral 1. The sample tube, indicated by numeral 2, holds a sample therein and is also termed a rotor. The tube 2 is inserted in a sample spinning mechanism (stator) 3 having an air bearing and is spun at high speed using a gaseous medium such as compressed air or nitrogen gas.

A movable mechanism 4 such as a toothed wheel is used to vary the angle of the stator 3. A shaft 5 or the like is connected to the movable mechanism 4 to permit the movable mechanism 4 to be controlled from the outside. A knob 6 that is connected with the shaft 5 is accessed and manipulated by a user when the magic angle is actually adjusted.

Chemical shift anisotropy can be eliminated and the NMR spectral linewidth can be sharpened by spinning the sample tube at the magic angle of 54.7° to the static magnetic field $B_0$. Therefore, adjustment of the magic angle has become an important technique.

In recent years, semiconductor thin-film growth technology has evolved. As a result, attempts to evaluate the physical properties of a thin-film sample on a wafer by investigating the film by solid-state NMR spectroscopy have begun. Its most fundamental method consists of scraping off the thin-film sample from the supporting basic material, loading the sample into a sample tube, and investigating the sample by an ordinary solid-state NMR spectrometer (non-patent document 1). In this method, however, the film is processed and, consequently, the reliability of the obtained data tends to be questioned.

Accordingly, a special solid-state NMR spectrometer capable of performing in-situ high-resolution solid-state NMR measurements without destroying thin-film samples such as semiconductor wafers have been proposed (patent document 1). Since this technique is important and provides a basis of the present invention, it is now summarized by referring to drawings.

FIG. 2 shows a high-resolution solid-state NMR spectrometer disclosed in JP-UM-A-62-79151, the spectrometer being adapted for measurements of wafers. The instrument has a magnet 11 that produces a static magnetic field $H_0$ in which a sample holder 12 having a sample-holding surface tilted at an angle of about 35.3° to the magnetic field is disposed. A sample 13 shaped like a circular disk similar to the sample holder 12 is placed on the holder 12. A rotatable shaft 14 is mounted to the holder 12 and supported by an air bearing 16 to which pressurized air is sent from a compressor 15. Plural grooves 17 are formed in the outer surface of the shaft 14. A nozzle 19 is attached to one end of the air bearing 16 to permit a rotating force to be applied to the shaft 14 when pressurized air from another compressor 18 is blown against the grooves 17 in the shaft 14. Therefore, the sample holder 12 is spun at high speed while the tilt angle of about 35.3° to the static magnetic field is maintained.

A transmit/receive coil 21 is attached at the front end of an arm 20 and located in close proximity to the center of spinning of the sample 13 that is spun at high speed together with the holder as described previously. The arm 20 is rotatably mounted to a support base 22. A transmitter circuit 23 supplies excitation pulses to the transmit/receive coil 21. A receiver circuit 24 is used to extract a resonance signal induced in the transmit/receive coil 21. The extracted resonance signal is processed by a computer 25.

In this configuration, since the sample 13 is spun on the surface that is tilted at an angle of about 35.3° to the static magnetic field, the axis of spinning is tilted at an angle of about 54.7° to the magnetic field, i.e., set to the magic angle.

A pulse sequence (excitation pulses) is sent from the transmitter circuit 23 to the transmit/receive coil 21 on the sample surface placed in proximity to the center of spinning such that the sample is irradiated with the pulse sequence. After the irradiation, a resonance signal induced in the transmit/receive coil 21 is taken from the receiver circuit 24. Thus, an NMR measurement can be made of a portion of the sample surface lying around the center of spinning.

If the transmit/receive coil 21 is moved along the rotating sample surface, NMR measurements can be made of an annular region extending along a circle of an appropriate radius from the center of spinning.

PRIOR ART REFERENCES

Patent Documents

Patent document 1: Published Japanese Utility Model No. S62-79151

Non-patent Documents

Non-patent document 1: Yasuto Noda et al., 7Li Microcoil MAS NMR Application to Cathode Materials for Thin-film Lithium Ion Batteries, 51st ENC (2010).

Among the prior art methods of solid-state NMR spectroscopy of thin films on substrate surfaces, the most common method consists of scraping off a thin-film sample from its supporting basic material and loading the sample into a sample tube. However, in the method of loading a sample into a cylindrical sample tube having small diameter and made of a ceramic, the tube acting also as a rotor, it is impossible to investigate the sample while the thin-film shape is maintained. Therefore, there is the problem that interesting physical properties that would be obtained when a substance or a composite material assumes the form of a thin film or a laminate film are lost.

The configuration of the technique disclosed in patent document 1 is similar to the configuration of the present invention. However, patent document 1 does not present data indicating the feasibility (e.g., obtained NMR spectra and information about amounts of samples, substrate sizes, sample spinning rates, and so on), and fails to present constituent elements necessary for modern high-resolution solid-state NMR spectroscopy implemented based on the premise that the spinning rate is at least 10 kHz. Although the configuration of patent document 1 has been devised by a company to which some of the present inventors belong, this technique is not yet put into practical use because of the problem described above.

In the technique of patent document 1 directed to measurements of samples in the form of thin film, a disklike sample holder is mounted to an end surface of a ceramic rotor. One surface of the holder is used as a sample-holding surface. A sample in the form of a flat sheet is stuck to the holding surface. However, patent document 1 does not make any mention of the method of sticking the sample. Furthermore, any technique of detachably mounting the sample holder to the rotor is not disclosed.

In addition, the technique of patent document 1 has a fatal defect. That is, the NMR transmit/receive coil of patent document 1 can measure only the inside of the transmit/receive coil. Furthermore, if the transmit/receive coil is located off the center of spinning, the measured region is annular and thus a correct high-resolution NMR spectrum cannot be obtained. If it is estimated from a figure of patent document 1 regarding the size of the NMR transmit/receive coil, the amount of sample, and the size of the substrate that the rotor diameter and the transmit/receive coil are substantially identical in size, the amount of the sample is very small and so the signal intensity is estimated to be quite small, taking account of the facts that the sample is thin and the diameter of the surface area is substantially identical to the rotor diameter and that the NMR signal intensity is generally in proportion to the amount of sample.

In order to spin the rotor at an ultrahigh speed of 10 kHz, it is necessary to achieve a high degree of balance. Consequently, the rotor is fabricated by an advanced machining technique and thus is expensive. Hence, the rotor is not a disposable part. On the other hand, where a rotor is repeatedly used, it is etched with an acid or an alkali after a measurement. Then, cleaning with an organic solvent or water needs to be repeated. This requires much labor. Preferably, the rotor is designed as a disposable unit. Any technique capable of solving these conflicting problems has not been disclosed.

SUMMARY OF THE INVENTION

In view of the foregoing, it is an object of the present invention to provide a high-resolution solid-state NMR spectrometer having a low-cost, disposable sample-holding portion permitting a disklike sample, which is so large that it cannot be inserted into an ordinary sample tube, to be measured intact.

This is achieved by a quite simple structure in which a sample holder for installation of a thin-film sample is placed in an end-portion of a rotor that is used in a conventional NMR sample tube module. RF pulse irradiation and detection of NMR signals are enabled by placing a surface coil in proximity to a thin-film sample, the coil being mounted on an RF circuit substrate for tuning and matching for an RF magnetic field applied to the rotating sample. An advantage of the shape of the surface coil is that laser light can be directed at the surface of the thin film from a direction normal to the surface through a central space. An experimental system for obtaining information about the molecular structure related to a physical property of the thin film can be built by exploiting the advantage and utilizing a combination with an external field that varies a physical property of the thin film.

This object is achieved by a solid-state NMR spectrometer associated with the present invention, the spectrometer having a stator placed within a static magnetic field and including an air bearing and a cylindrically shaped rotor holding a sample and disposed in the stator. RF excitation pulses are directed to the sample from a transmit coil while spinning the rotor at high speed about an axis tilted at an angle of about 54.7° (i.e., the magic angle) to the static magnetic field to obtain a solid-state NMR spectrum. The rotor has a one-end portion in which an engaging mechanism is mounted to permit a sample holder holding the sample to be detachably held. A coil holder that holds the transmit coil is so designed that the position of the sample holder mounted to the one-end portion of the rotor and the position of the transmit coil can be adjusted.

In one feature of the spectrometer, the sample holder has a disklike sample-holding portion that may or may not have an internal cavity. The sample is placed on the surface of the sample holder or received in the internal cavity. Furthermore, the sample holder has a pillar portion mounted in a central portion of the rear surface of the disklike sample-holding portion. The sample holder is mounted to the one-end portion of the rotor by the engaging mechanism via the pillar portion.

In another feature of the spectrometer, the transmit coil is substantially identical in diameter to the disklike sample-holding portion.

In a further feature of the spectrometer, the disklike sample-holding portion is spun at high speed on a plane that is tilted at about 35.3° to the static magnetic field.

In an additional feature of the spectrometer, when the sample is a thin film, it is placed on the surface of the disklike sample-holding portion.

In a yet other feature of the spectrometer, when the sample assumes a powdered form, it is loaded in the internal cavity of the disklike sample-holding portion.

A sample holder associated with the present invention is a sample holder adapted for use in the solid-state NMR spectrometer and has a disklike sample-holding portion and a pillar portion formed in a central portion of the rear surface of the disklike sample-holding portion which may or may not have an internal cavity. The sample is placed on the surface of the disklike sample-holding portion or received in the internal cavity. The sample holder is mounted to the one-end portion of the rotor via the pillar portion by the engaging mechanism.

A method of solid-state NMR spectroscopy associated with the present invention makes it possible to obtain solid-state NMR spectra using the solid-state NMR spectrometer.

During the solid-state NNR spectroscopy, the sample held on the sample holder is irradiated with, or subjected to, at least one type of laser light, microwaves, heat waves, hot air, cold air, and electric power supplied via a wireless power feeding coil.

The solid-state NMR spectrometer according to the present invention has the stator placed within the static magnetic field and including the air bearing and the cylindrically shaped rotor holding a sample and disposed in the stator. RF excitation pulses are directed at the sample from the transmit coil while spinning the rotor at high speed about the axis tilted at an angle of about 54.7° (i.e., the magic angle) to the static magnetic field to collect a solid-state NMR spectrum. The rotor has the one-end portion in which the engaging mechanism is mounted to permit the sample holder holding the sample to be detachably held. The coil holder that holds the transmit coil is so designed that the position of the sample holder mounted to the one-end portion of the rotor and the position of the transmit coil can be adjusted. Consequently, a solid-state NMR spectrometer permitting a disklike sample, which is so large that it cannot be put into an ordinary sample tube, to be measured intact is offered.

Furthermore, according to the method of solid-state NMR spectroscopy of the present invention, solid-state NMR spectra are obtained by the use of the solid-state NMR spectrometer and, therefore, a method of solid-state NMR spectroscopy can be offered which permits a disklike sample that is so large that it cannot be put into an ordinary sample tube to be measured intact.

DETAILED DESCRIPTION OF THE INVENTION

The present invention is intended to make high-resolution solid-state NMR measurements of a single sample in the form of a thin film at high sensitivity without peeling off the sample from its backing material and without deforming the thin film.

In the related art, a special device having a rotatable sample holder integrated with a rotary mechanism has been required. In contrast, in the present invention, a shaft used to rotate a sample holder for attachment of a thin-film sample is fitted as an attachment in a sample hole formed in a rotor used in the related art NMR sample tube module. As a result, the object can be achieved with a quite simple structure.

A surface coil mounted on an RF circuit substrate for tuning and matching for an RF magnetic field applied to the rotating thin film is placed in close proximity to the sample. Consequently, the S/N of the NMR signal can be optimized. RF pulse irradiation and observation and detection of the NMR signal can be done.

In modern high-resolution solid-state NMR spectroscopy, the sample spinning rate is required to be in excess of 10 kHz (600,000 rpm). Under this condition, if the center of gravity deviates slightly, the spinning rate of the sample tube will drop in many cases. Accordingly, when the sample tube is designed, its degree of rigidity (density, length, radius, wall thickness, and concentricity) is regarded as quite important in determining the performance.

Accordingly, it is emphasized here that a technique of spinning a sample while attaching something to the sample tube falls outside the category of the normal measurement method. We have considered that the reason why the sample spinning rate cannot be increased is low rigidity of the microsample tube (glass capillary). That is, the ratio of the length of the glass capillary (L/D) to its diameter is larger. This induces a precession, thus hindering the spinning of the sample.

Accordingly, we conducted experiments on the assumption that when a sample holder greater in size than the microsample tube is attached, the sample would be spun at high speed unless the L/D of the cylindrical portion supporting the holder is large enough to prevent precession of the holder. When a sample holder having a diameter of 7 mm was attached to a rotor (sample tube) having a diameter of 4 mm, a spinning rate of about 13 kHz was achieved. When a sample holder having a diameter of 12 mm was attached, a spinning rate of about 7 kHz was achieved.

Embodiment 1

The essential components for implementing the present invention are a "sample holder" and a "surface coil". These are mounted as attachments to a unit of a related art high-resolution solid-state NMR spectrometer. As a result, high-resolution solid-state NMR spectroscopy of thin samples can be carried out.

(1) Sample Holder

Figure 1:
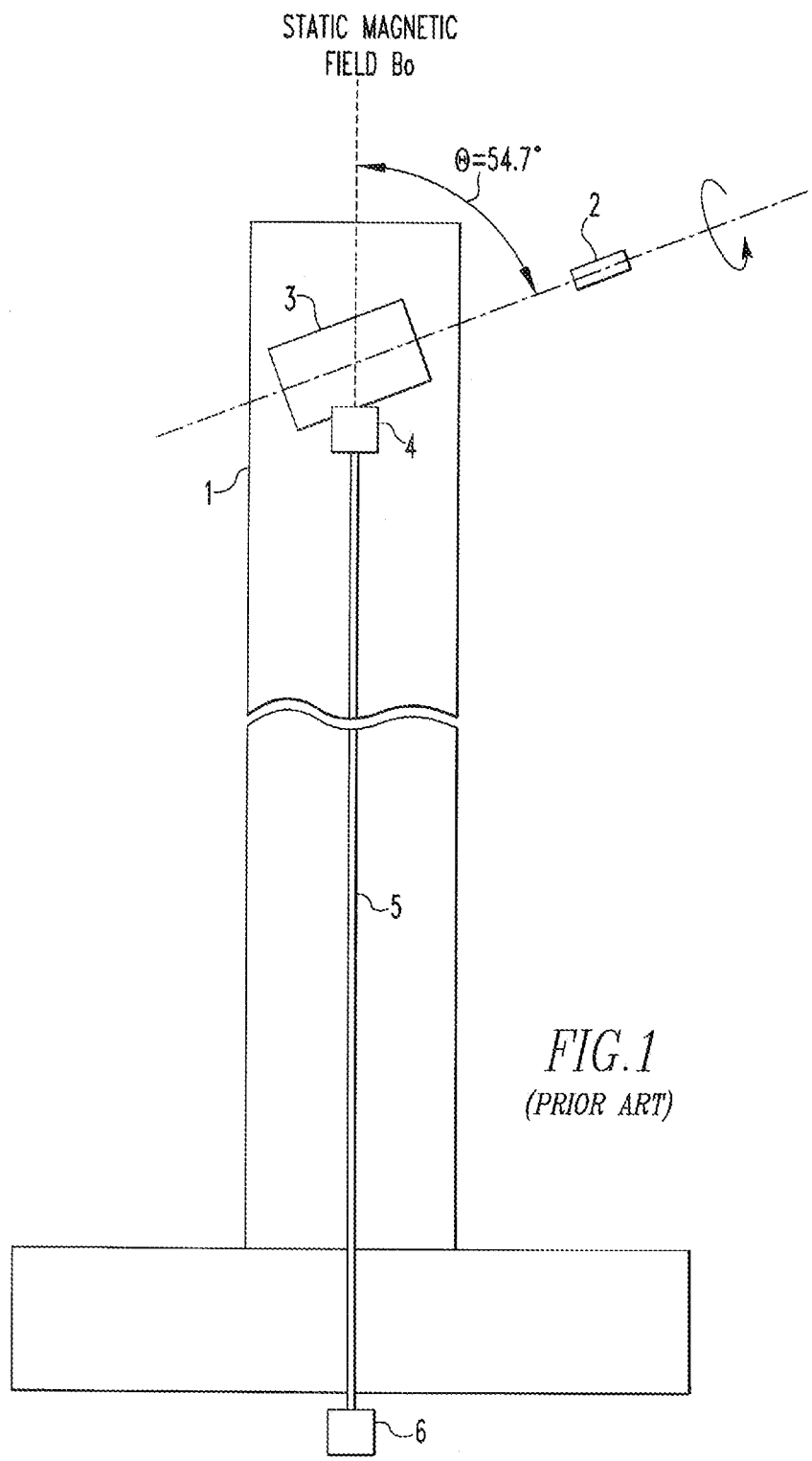
FIG. 1 is a front elevation of a related art solid-state NMR spectrometer.
Figure 2:
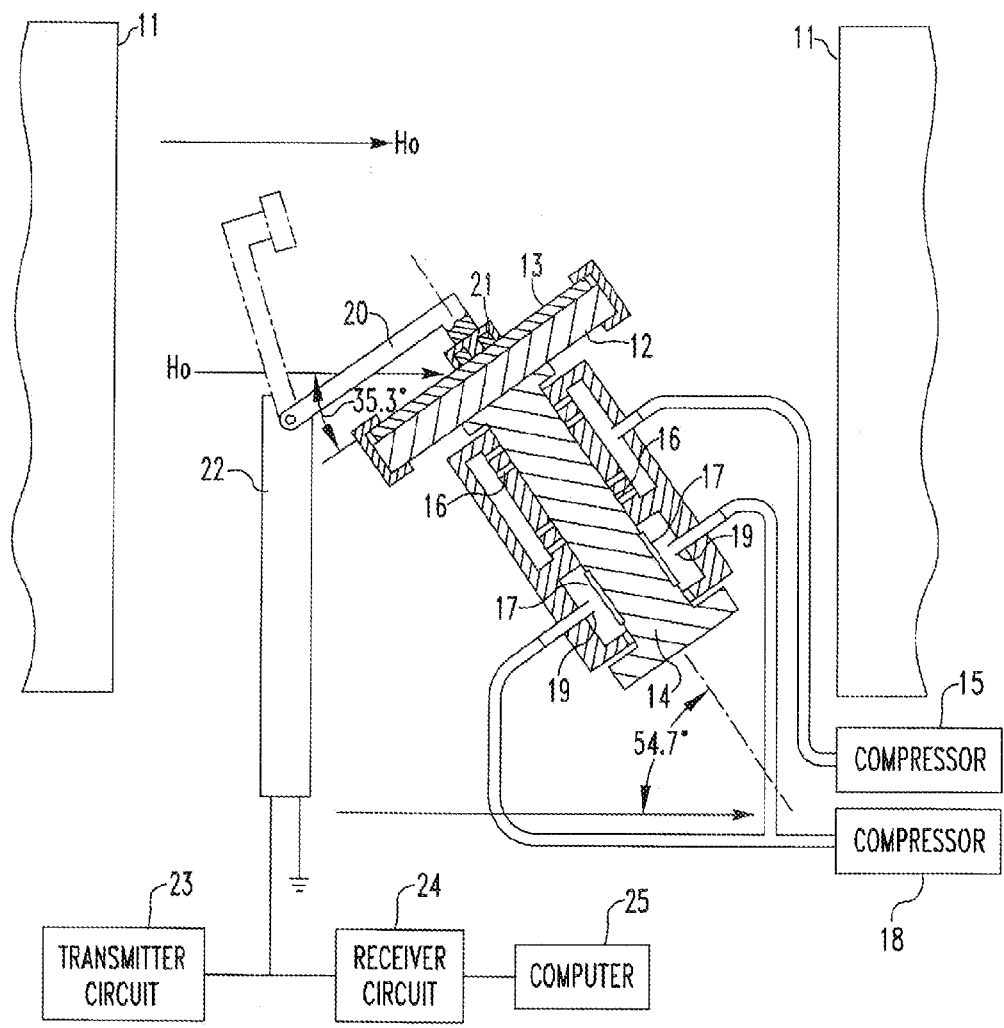
FIG. 2 is a front elevation, partly in cross section and partly in block form, of a related art solid-state NMR spectrometer for measurements of wafers.
Figure 3:
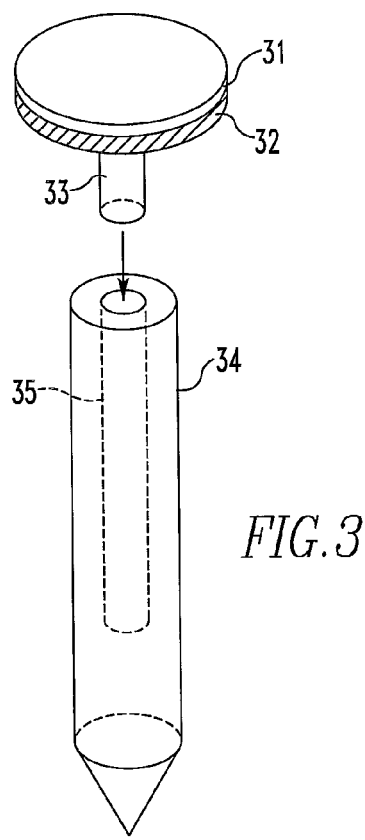
FIG. 3 is an exploded perspective view of a sample holder associated with the present invention, the holder being used for solid-state NMR measurements.

An actually fabricated sample holder for installation of a thin-film sample and a sample tube for solid-state NMR spectroscopy are shown in FIG. 3, the holder being attached to the sample tube. The sample holder, indicated by numeral 32, assumes a disklike form and has a convex portion 33 in the center of the lower surface. A circular sample 31 cut out in conformity with the diameter of the sample holder is stuck to the upper surface via an appropriate adhesive. A commercially available sample tube (rotor) 34 for solid-state NMR spectroscopy has a diameter of 4 mm and a concave portion 35 into which a sample would normally be inserted. The manner in which the convex portion 33 of the sample holder 32 is fitted and held in the concave portion 35 such that the holder 32 and the sample tube 34 are detachably joined together are shown.

The sample holder may be fitted to the upper end of the sample tube 34 like a cap such that both are separably joined together. Furthermore, if both are threadedly engaged together, they can be integrated together more certainly than where they are fitted together. In this way, the method of engaging and joining the sample holder to the sample tube can assume various modifications. The shapes, dimensions, and materials of the experimental prototypes were as follows.

shape: circular form
    dimensions
        diameter: 7 mm
        thickness: 0.5 mm to 2 mm
    material: Delrin (Trademark Registered)
    notes: A thin-film sample was obtained by vapor depositing a thin film of aluminum on a quartz substrate. The sample was stuck to the upper surface of the sample holder via an instantaneous adhesive such as Aron Alpha (Trademark Registered). The sample holder was held to the sample tube 34 simply by fitly inserting the convex portion 33 of the holder into the recessed portion 35 of the sample tube 34.

In each experiment, a thin-film sample could be spun while placing the sample on the holder up to 11 kHz, beyond which the material (Delrin (™)) of the holder was stretched by the effect of the centrifugal force. Stress was applied to the substrate, destroying it. If a harder and lighter material (preferably, ceramics) is used as the material of the holder, further improvement of the spinning rate will be expected. Furthermore, it is expected that experimental conditions giving higher resolutions will be established.

We succeeded in spinning a thin film of metal aluminum at a high rate of 7.5 kHz within a magnetic field of 7 tesla. This shows that high-resolution solid-state NMR measurements of thin metal films are enabled. In addition, other applications such as successive analysis of a metal corrosion process are expected.

(2) Surface Coil

A surface coil is fabricated by winding copper wire into a circular form within the same plane. The shape is preferably a circular form in order to enhance the RF magnetic field intensity and RF magnetic field homogeneity. A rectangular surface coil can also be used. In each experimental prototype, the surface coil was attached to one surface of a circular circuit substrate. An RF circuit for tuning and matching the surface coil was mounted on the other surface.

Figure 4A:
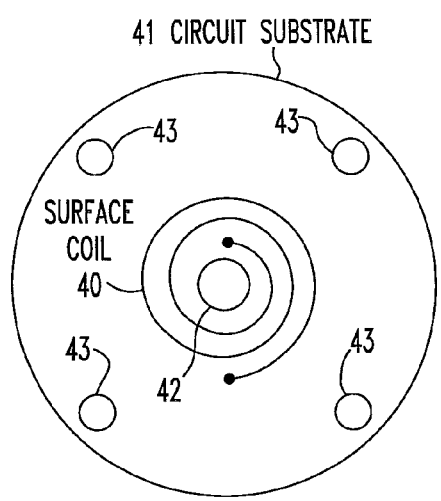
FIGS. 4A and 4B are plan views of a detection coil associated with the invention, the coil being for use in solid-state NMR measurements.
Figure 4B:
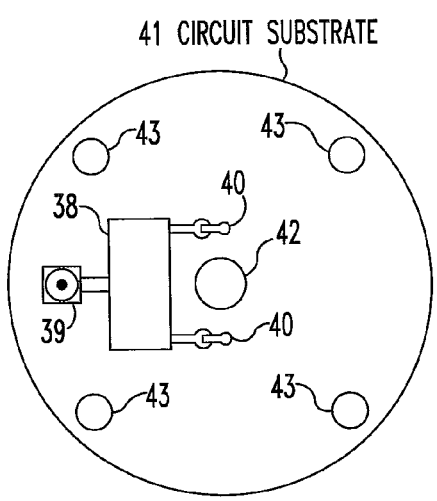

FIGS. 4A and 4B show a circuit substrate 41 on which a surface coil 40 is mounted. FIG. 4A shows the surface on which the coil 40 is mounted. FIG. 4B shows the surface on which an RF circuit 38 for tuning and matching for applied RF waves is disposed. Both terminals of the surface coil 40 are connected to the RF circuit 38. The substrate 41 is centrally provided with a through-hole 42. Four holes 43 through which set screws are passed are formed around the outer periphery. The surface coil 40 is mounted to the substrate 41 such that the through-hole 42 is located in the center. Both ends of the coil pass through the substrate 41 and are connected with the RF circuit 38 on the rear surface. A connector 39 is used to connect the RF circuit 38 and surface coil 40 with an external circuit. The surface coil used for the experiments had a diameter of 7 mm and a wire diameter of 0.5 mm. The coil had 2.5 turns of wire. The inductance was 84.5 nH. The Q value was 40 (281.8 MHz). The surface coil 40 is annular in shape in FIGS. 4A and 4B. Obviously, the surface coil can be shaped rectangularly, solenoidally, or otherwise.

Figure 5:
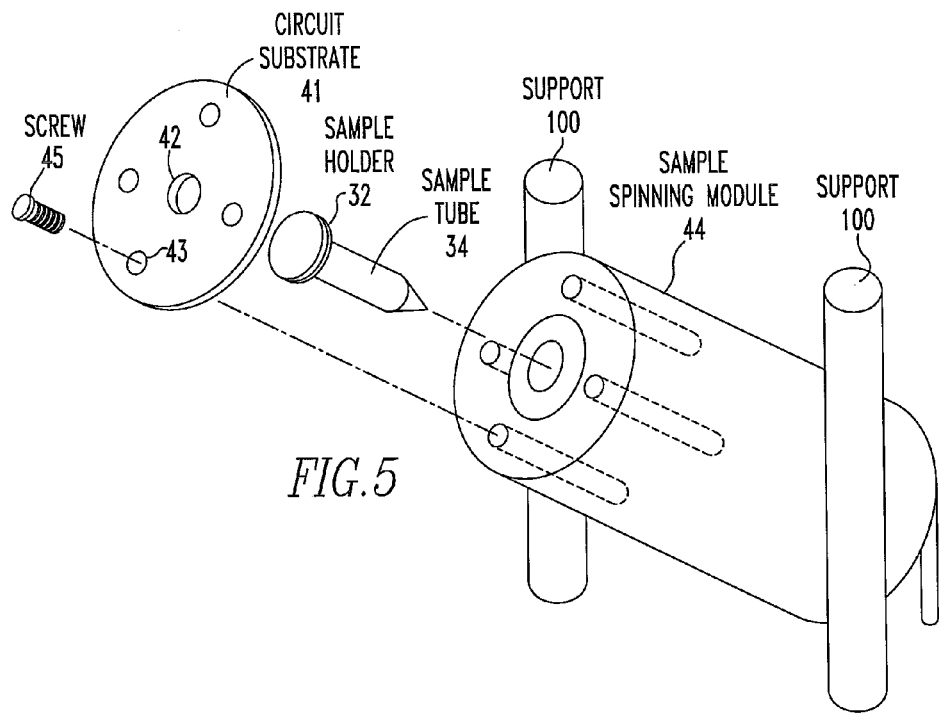
FIG. 5 is an exploded perspective view of a solid-state NMR measurement portion associated with the invention.

(3) Parts Configuration for Adjusting the Position of the Surface Coil relative to the Sample FIG. 5 conceptually illustrates the manner in which the sample holder 32 associated with the present invention and the circuit substrate 41 holding the surface coil 40 are mounted to a sample spinning module 44 having a stator provided with an air bearing that is a unit of the related art high-resolution solid-state NMR spectrometer.

The sample tube 34 (see FIG. 3) to which the sample holder 32 holding the sample 31 is mounted is inserted into the sample spinning module 44 placed within the static magnetic field. The module 44 is held to two support pillars 100 such that the axis of spinning is tilted at the magic angle to the static magnetic field. The substrate 41 is so disposed that the surface coil 40 faces the sample 31 exposed from the spinning module 44. The substrate 41 is directly held to the spinning module 44 by a screw 45. Because the surface coil 40 is placed in close proximity to the sample surface, NMR measurements are permitted. The distance between the surface coil and the thin-film sample is adjusted by the screw 45 which acts also to hold the substrate 41.

A commercially available sample tube was used as this experimental prototype. Because blades against which high-pressure gas is blown to obtain a rotating force are mounted to a lower portion of the sample tube (rotor), the sample holder is mounted to an upper portion relatively smoothly. In the case of another commercially available sample tube whose blades are mounted to an upper portion of a rotor, the sample holder can be mounted because the blades are centrally provided with a hole.

Measurements can be performed similarly to the case of ordinary high-resolution solid-state NMR measurements. That is, it is assumed that a standard high-resolution solid-state NMR system is used, the system including a spectrometer system, an NMR probe for placing a sample in a magnetic field, a sample-spinning system for obtaining a high-resolution spectrum by spinning the a solid powdered sample (thin film, in this example), and a preamplifier for amplifying the NMR signal. A control computer, a transmitter, and a receiver are integrated in the spectrometer system. The NMR probe includes a power amplifier, a duplexer, and electric circuitry for applying RF pulses to the sample.

Figure 6:
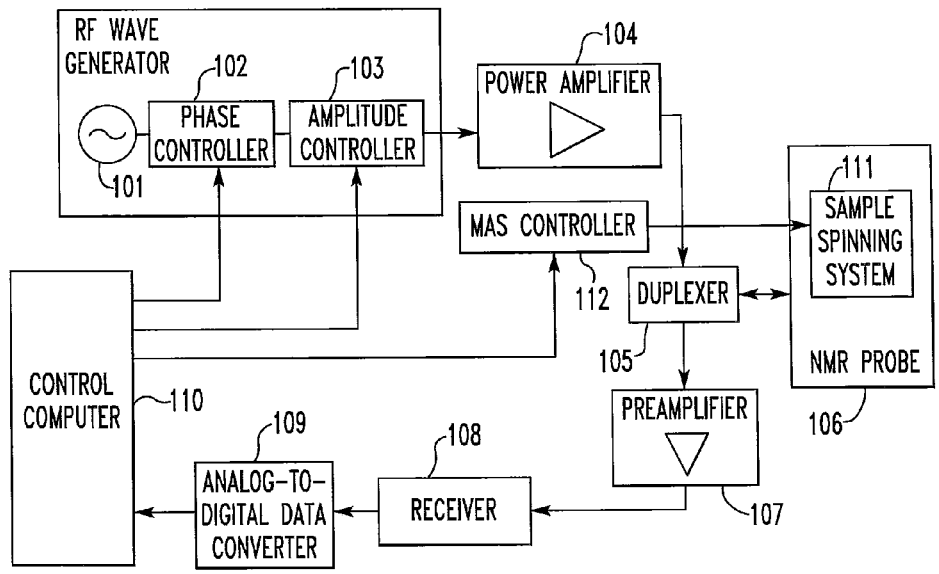
FIG. 6 is a block diagram of a solid-state NMR spectrometer associated with the invention.

The high-resolution solid-state NMR system is schematically shown in FIG. 6. RF waves generated by an RF wave generator 101 are controlled in terms of phase and pulse width by a phase controller 102 and an amplitude controller 103 and sent as RF pulses to a power amplifier 104.

The RF pulses amplified to a power level necessary to excite an NMR signal by the power amplifier 104 are fed to an NMR probe 106 via a duplexer 105 and then applied to the sample to be investigated from a transmit/receive coil (not shown) inside the sample spinning system placed in the NMR probe 106.

After the RF pulse irradiation, a feeble NMR signal generated by the sample is detected by the transmit/receive coil and sent via the duplexer 105 to a preamplifier 107, where the signal is amplified to a signal intensity that can be handled by a receiver 108.

The receiver 108 converts the RF NMR signal amplified by the preamplifier 107 into an audio frequency that can be converted into a digital signal. At the same time, the receiver 108 controls the amplitude. The NMR signal that has been converted into the audio frequency by the receiver 108 is converted into a digital signal by an analog-to-digital data converter (A/D converter) 109 and sent to a control computer 110.

The control computer 110 controls not only the phase controller 102 and the amplitude controller 103 but also a sample spinning system 111 within the NMR probe 106 via a magic angle spinning (MAS) controller 112.

Figure 7:
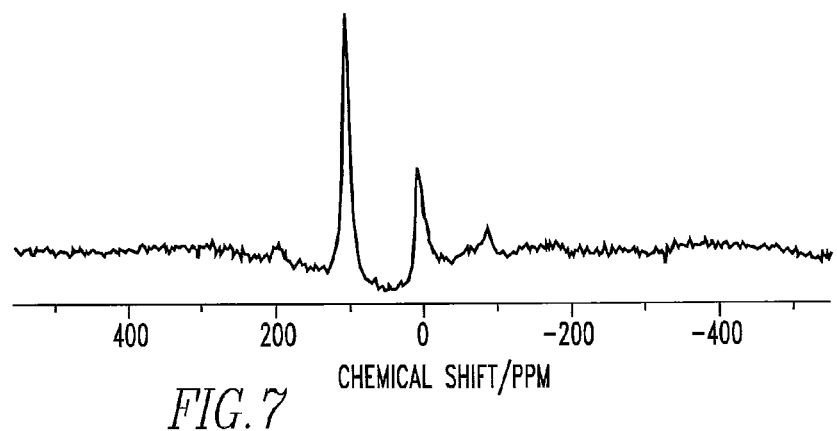
FIG. 7 is an NMR spectrum actually obtained by a solid-state NMR spectrometer of a sample according to the invention.

A high-resolution solid-state NMR spectrum actually obtained using the present instrument is shown in FIG. 7. This spectrum is a $^{27}$Al MAS NMR spectrum of a thin film of aluminum metal obtained by high-resolution solid-state NMR spectroscopy. The spinning rate was 7.4 kHz. The carrier frequency was 7.8 MHz. The accumulation time was about 12 hours.

Embodiment 2

Figure 8:
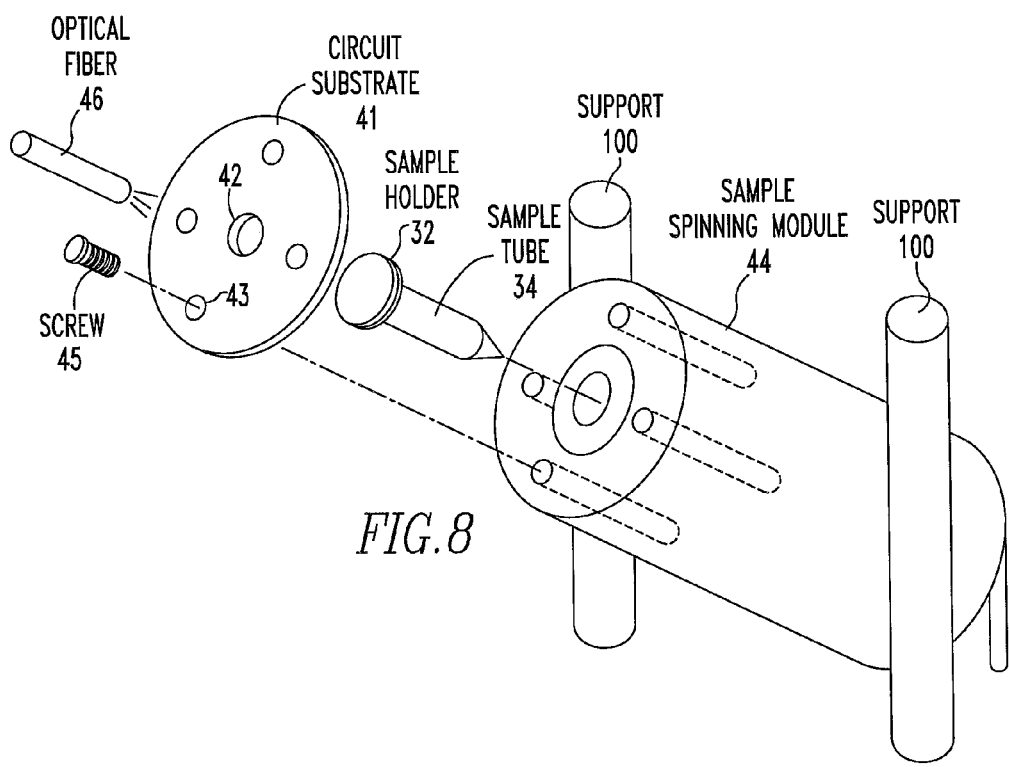
FIG. 8 is an exploded perspective view of another solid-state NMR measurement portion associated with the invention.

The present invention can also be applied to solid-state NMR measurements combined with light as illustrated in FIG. 8. That is, NMR experiments can be performed while activating photoinduction of a functional material. Also, a combination with spectroscopy utilizing a quite different energy region of light is possible.
(1) Configuration The sample tube 34 to which the sample holder 32 is mounted is inserted into the sample spinning module 44 and the substrate 41 is mounted to the spinning module 44 in the same way as in the example of FIG. 5.

As shown in FIG. 8, light is directed at a sample in the form of a thin film on the sample holder 32 by an optical guide system including an optical fiber 46, reflecting plates, a collimator, and other parts from the direction of the axis of spinning of the sample. The substrate 41 interposed between the optical fiber 46 and the sample holder 32 has the through-hole 42 in a central portion of the surface coil. Since there is no conductor, the light is not blocked. Accordingly, the light is directed through this through-hole 42.

Figure 9:
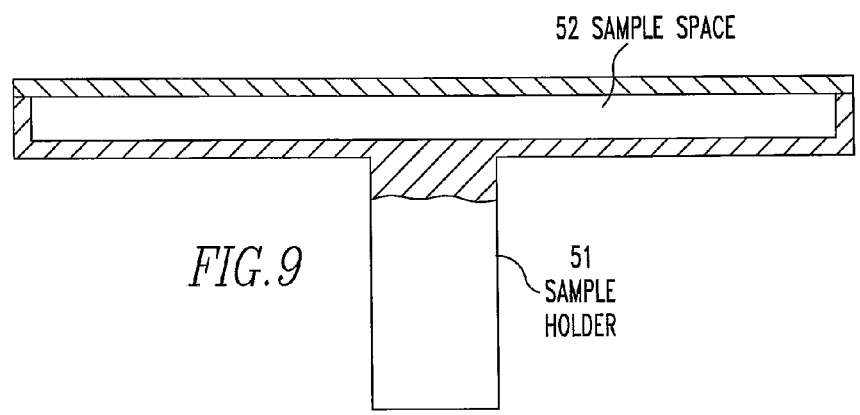
FIG. 9 is a vertical cross section of another sample holder associated with the invention, the holder being used for solid-state NMR measurements.

In the case of a powdered sample, as shown in FIG. 9, a transparent sample holder 51 which is made of quartz and which transmits light can be used. The holder 51 has a front-end portion in which a compressed, cylindrical sample space 52 is formed, the space 52 extending perpendicularly to the axis of spinning. A powdered sample can be investigated by loading the sample into the sample space, inserting and holding the holder in the sample tube, and spinning the holder at high speed.

(2) Operation

A structure having transitions brought about by optical chopping synchronized with the NMR system is detected by the surface coil. This is useful for analysis of new materials which are made to produce dynamic photoinduced phase transitions by optical chopping. Furthermore, the invention is useful for analysis of materials such as resist materials that act on light. In the related art instrument, it has been difficult to spin a sample at high speed while efficiently irradiating the sample with light. According to the invention, the sample is thin and has a large surface area. Therefore, it is possible to irradiate the sample with light efficiently. Furthermore, the sample can be spun at high speed.

Embodiment 3

Figure 10:
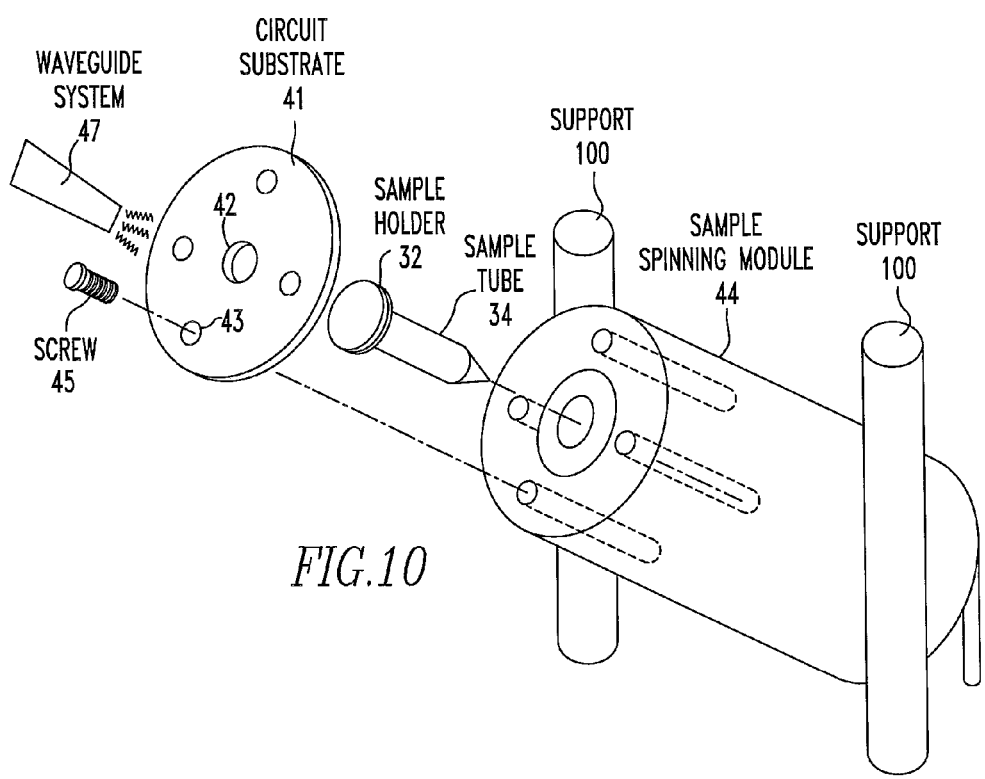
FIG. 10 is an exploded perspective view of a further solid-state NMR measurement portion associated with the invention.

The present invention can also be applied to solid-state NMR spectroscopy combined with microwaves (μwaves) as shown in FIG. 10.
(1) Configuration The sample tube 34 to which the sample holder 32 is mounted is inserted into the sample spinning module 44 and the substrate 41 is mounted to the spinning module 44 in the same way as in the example of FIG. 5.

A thin-film sample is irradiated with microwaves by a waveguide system 47 (such as a microwave waveguide or a microwave resonator) for microwaves through milliwaves to terahertz waves in such a way that the waves do not spatially interfere with the sample holder 32, substrate 41, and sample spinning module 44. Because the substrate 41 has the through-hole 42 in the central portion of the surface coil, and because there is no conductor, the microwaves are not directly blocked. Accordingly, the microwaves are applied to the sample via the through-hole 42.
(2) Operation Under microwave irradiation, variations in the NMR spectrum caused by variations in physical properties of the thin film are directly measured. The sensitivity near the surface can be enhanced by the effects of DNP (dynamic nuclear polarization).

Embodiment 4

Figure 11:
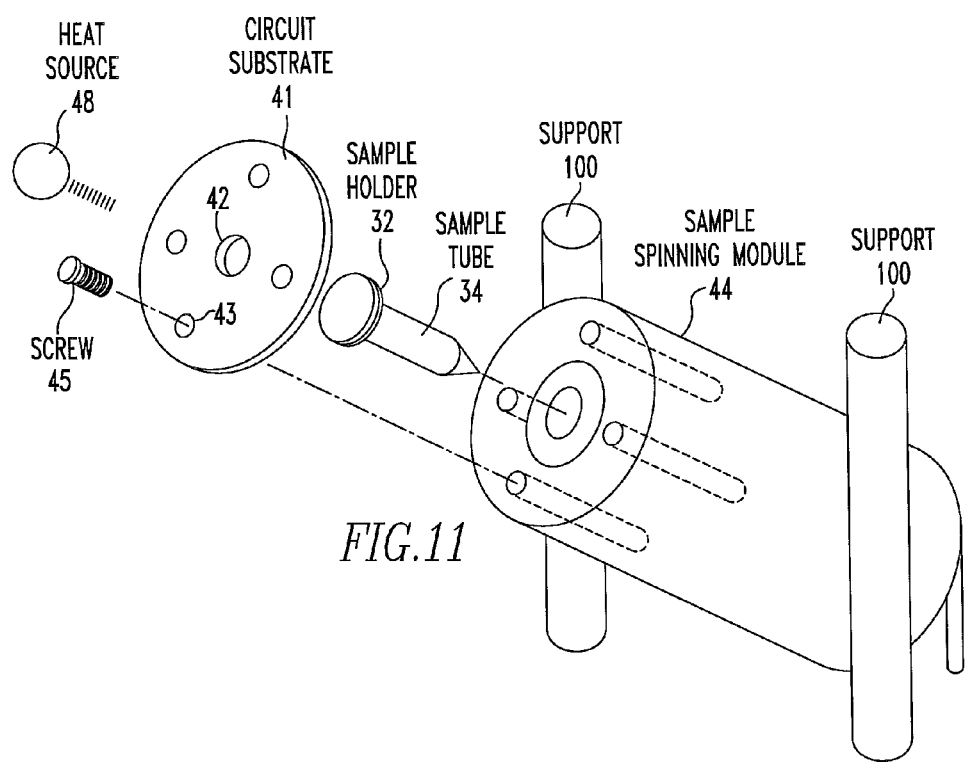
FIG. 11 is an exploded perspective view of a yet other solid-state NMR measurement portion associated with the invention.

The present invention can also be applied to solid-state NMR measurements used with heat as shown in FIG. 11. Temperature-variable NMR experiments can be carried out in a temperature range, which is difficult to realize with the related art probe, by directly varying the sample temperature.
(1) Configuration As shown in FIG. 11, a heat source 48 is placed over the sample holder 32. The sample is directly heated by heat rays or cooled. In this case, the material of the holder preferably has a small thermal conductivity. The substrate 41 has the through-hole 42 in the central portion of the surface coil. Since there is no conductor, the heat rays are not blocked out. Accordingly, the heat rays may be applied via the through-hole.
(2) Operation The sample can be heated by blowing warm air directly against the sample or by causing laser light to impinge directly on the sample. Furthermore, the sample can be cooled by spraying liquid nitrogen or liquid helium against the sample holder.

In none of conventional MAS experiments, samples are directly heated or cooled. Such direct heating or cooling is achieved first by the present invention in which the sample is exposed. Therefore, an NMR spectrum of a sample in a temperature range, where it has been heretofore difficult to make experiments, can be obtained. MAS spectra can be obtained while a spot on a sample is locally heated to 1,000° C. or higher by a laser heating method.

Since the whole experiment system including the sample tube does not need to be heated, high-resolution solid-state NMR measurements at high temperatures can be facilitated. It is expected that this will especially contribute to inorganic NMR spectroscopy.

Embodiment 5

Figure 12A:
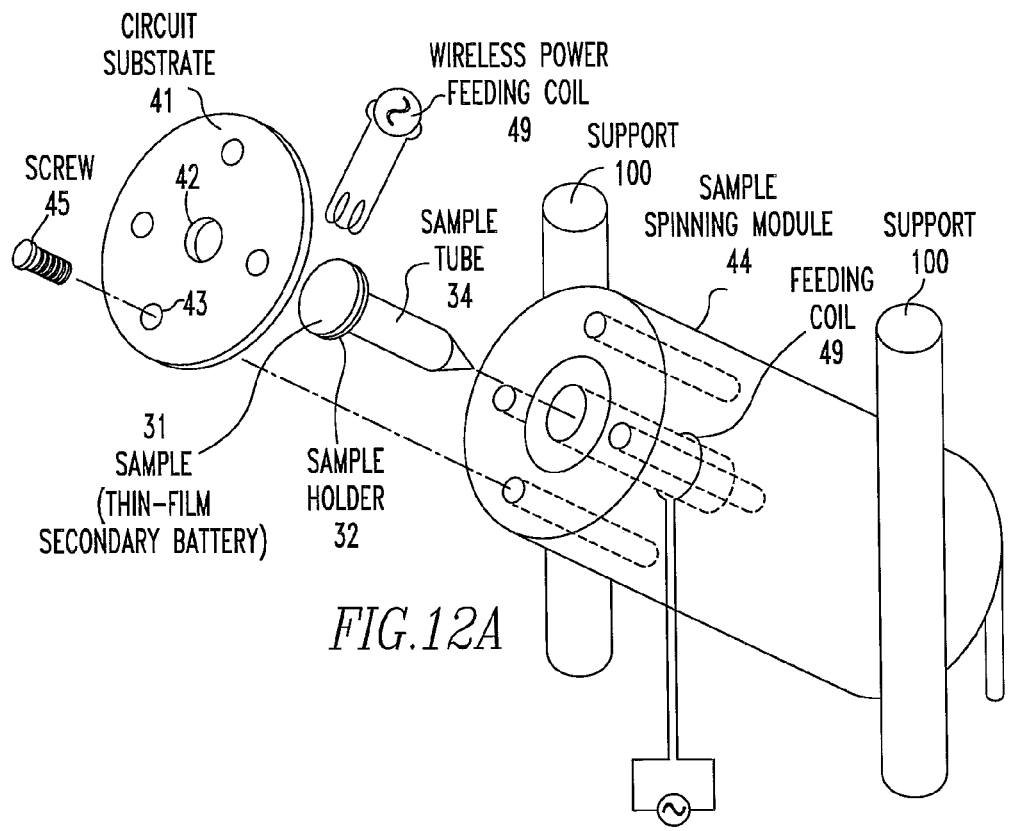
FIGS. 12A and 12B show a still other solid-state NMR measurement portion associated with the invention.
Figure 12B:
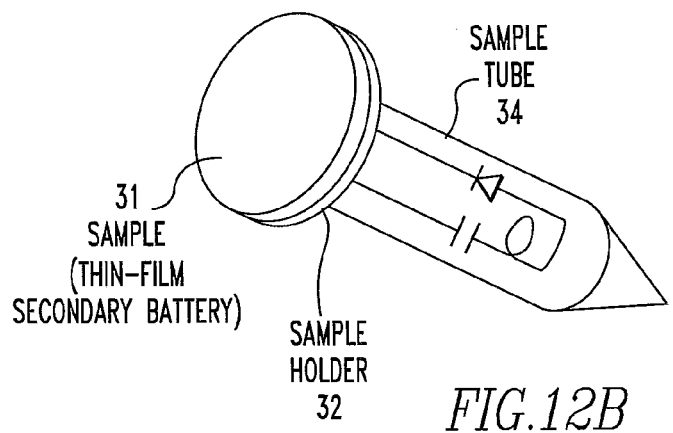

The present invention can also be applied to solid-state NMR measurements combined with batteries as shown in FIGS. 12A and 12B. When a thin-film secondary solid-state lithium battery is charging and discharging a sample, NMR measurements can be carried out.

(1) Configuration

As shown in FIG. 12A, a wireless power feeding coil 49 is mounted around a region in which the sample tube 34 of the sample spinning module 44 is inserted. As shown in FIG. 12B, a wireless power receiver circuit including a power receiving coil L for receiving electromagnetic waves from the coil 49, a diode for converting an alternating voltage developed across the coil L into a DC voltage, and a capacitor is mounted in the recessed portion 35 which would normally receive the sample in the sample tube 34. The wireless power receiver circuit is connected with the thin-film solid-state secondary lithium battery mounted on the sample holder 32 by electrical wires. A DC voltage is supplied from the wireless power receiver circuit to the sample such as the thin-film solid-state secondary lithium battery, thus charging the secondary battery. The wireless power feeding coil 49 does not need to be disposed within the sample spinning module 44. The coil may be disposed around the sample holder 32 or above the substrate 41. In this case, the power receiving coil L is preferably disposed within the holder 32 such that the coil L is well coupled to the coil 49. Where the coil 49 is disposed above the substrate 41, electrical power is supplied to the power receiving coil mounted on the sample holder via the through-hole 42 formed in the substrate 41.

(2) Operation

The wireless power feeding coil 49 connected with an AC power supply causes the wireless power receiver circuit disposed inside the sample tube to produce a DC voltage by mutual induction. The DC voltage is supplied to the thin-film solid-state secondary lithium battery carried on the sample holder, thus charging the battery.

Although in-situ NMR experiments during charging and discharging processes have been reported, magic-angle spinning that is essential for high-resolution solid-state NMR is not done, i.e., in a still state. In order to understand battery characteristics that are macroscopic natures from the microscopic level (i.e., from the atomic or molecular level), magic-angle spinning (MAS) NMR spectroscopy is necessary.

An NMR spectrum is highly sensitive to physical parameters (the mobility of lithium ions, electrical conductivity, variations in atomic valences of positive atoms during an oxidation-reduction process, and variations in electronic structure) directly related to the battery efficiency. Furthermore, NMR can selectively measure chemical elements and can be used for observations of elements directly participating in the battery operation. An NMR spectrum is sensitive to small variations in local structures and thus it is possible to nondestructively trace variations in structures caused by insertion and withdrawal of lithium ions.

An important characteristic of NMR is quantitativeness because the integral intensity of an NMR signal is in proportion to the number of nuclei resonating within a sample. Accordingly, if NMR spectra in individual phases can be separated, the proportions of the contained phases can be quantitatively estimated. As described so far, variations in local structures, atomic valences, and electronic structures caused by insertion and withdrawal of lithium ions can be quantitatively traced and the mechanism of deteriorating the battery characteristics can be studied by making measurements at high resolution while operating a lithium ion battery.

Embodiment 6

Figure 13:
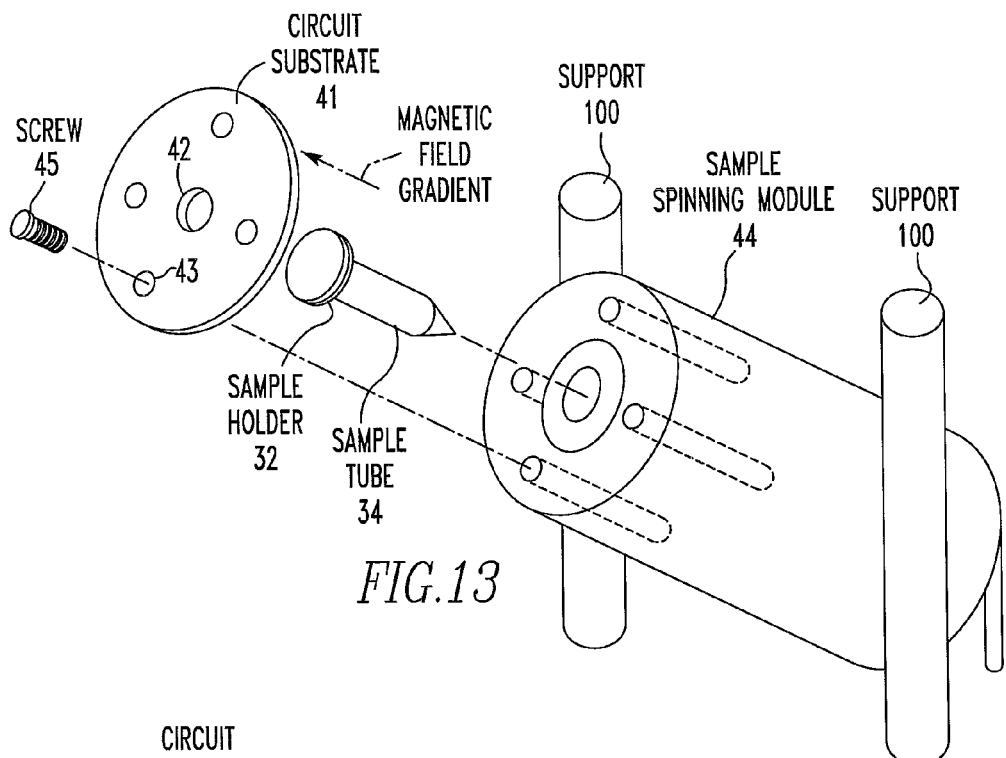
FIG. 13 is an exploded perspective view of an additional solid-state NMR measurement portion associated with the invention.

The present invention can also be applied to solid-state NMR measurements combined with magnetic field gradients as shown in FIG. 13. Nondestructive imaging of a thin film can be done.

(1) Configuration

A gradient coil (not shown) is arranged around the substrate 41 or the sample holder 32 to produce a gradient magnetic field tilted relative to the direction of axis of spinning of the sample in the sample tube as shown in FIG. 13. Consequently, positional information about the depths of the thin film can be reflected in the NMR spectrum.

(2) Operation

An NMR spectrum can be obtained under a constant gradient magnetic field when a constant current is fed to a gradient coil. Imaging information in the depthwise direction can be obtained when a gradient pulsed magnetic field is produced by energizing the gradient coil with a pulsed current.

Embodiment 7

Figure 14:
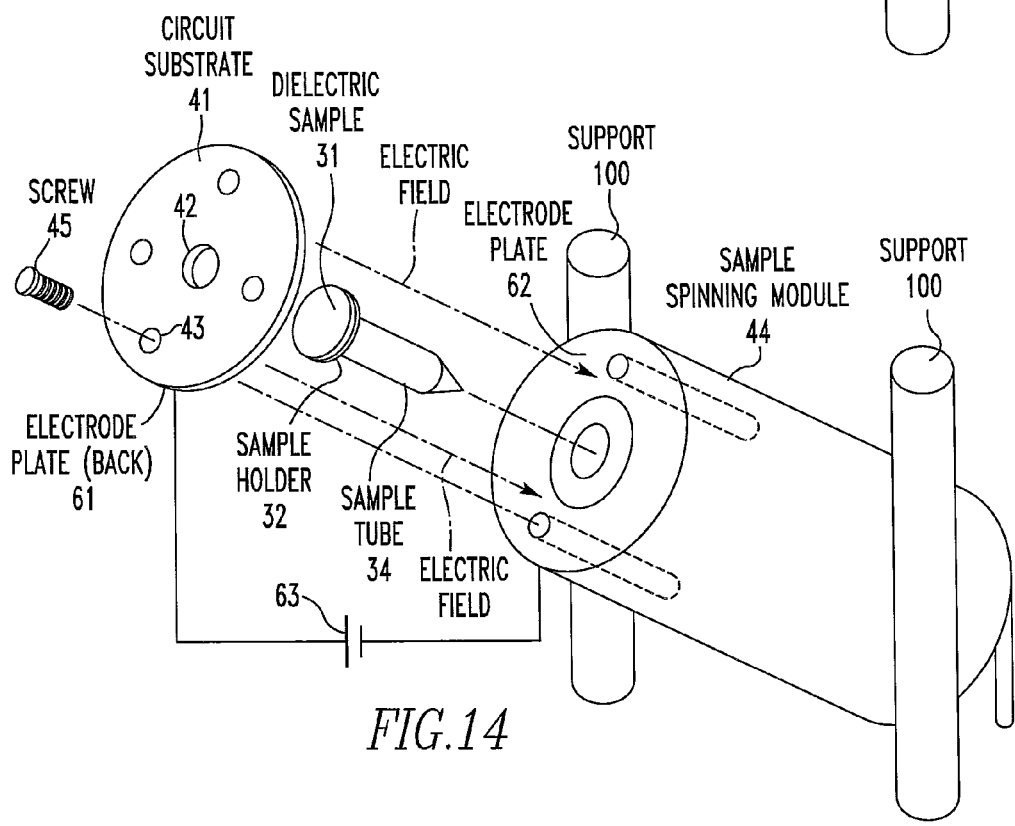
FIG. 14 is an exploded perspective view of a still other solid-state NMR measurement portion associated with the invention.

The present invention can also be applied to solid-state NMR measurements performed in combination with an electric field as shown in FIG. 14. High-resolution solid-state NMR measurements of dielectric materials can be carried out.

(1) Configuration

A dielectric sample 31 is mounted to the sample holder 32 and sandwiched between spatially separated electrode plates 61 and 62. One of the electrode plates is attached to the surface on which the surface coil 40 of the substrate 41 is mounted. The other is attached to the upper surface of the sample spinning module 44.

(2) Operation

The distance between the electrode plates is adjusted with a screw. A voltage is applied across the electrode plates from a DC power supply 63. Under this condition, high-resolution solid-state NMR measurements of dielectric substances are enabled by performing high-resolution solid-state NMR spectroscopy.

Embodiment 8

Figure 15:
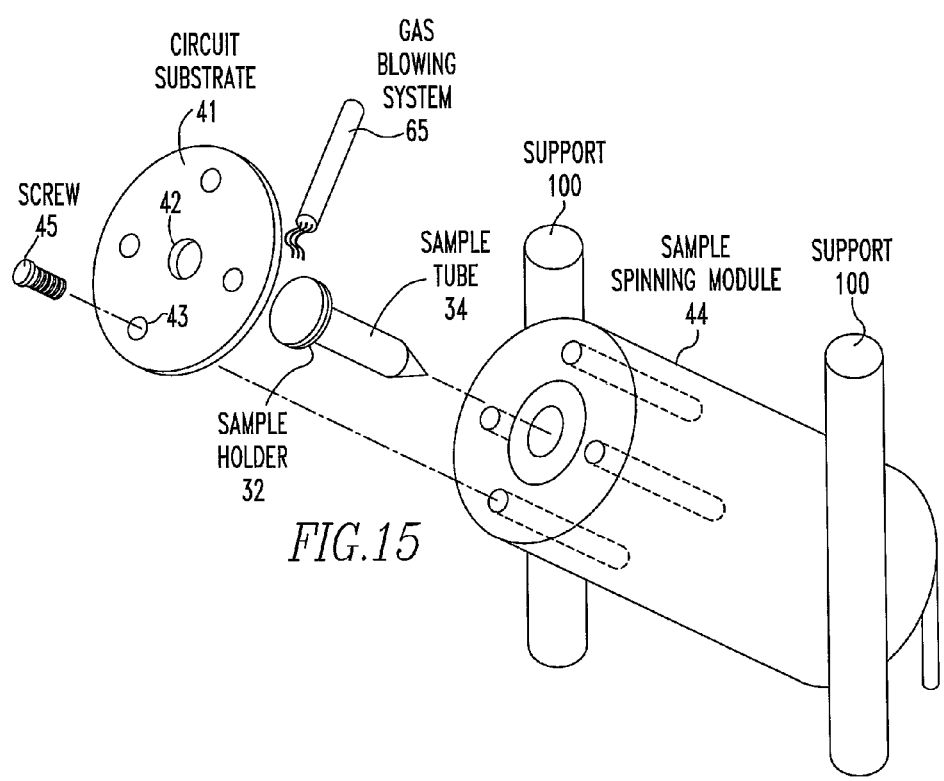
FIG. 15 is an exploded perspective view of a still further solid-state NMR measurement portion associated with the invention.

The present invention can also be applied to solid-state NMR measurements made in combination with a vapor-phase reaction as shown in FIG. 15. High-resolution solid-state NMR spectroscopy of porous thin-film materials can be performed.

(1) Configuration

A porous thin-film material is mounted as the sample 31 to the sample holder 32. A gas blowing system 65 is disposed around the sample holder 32 to blow gas against the surface of the sample. The gas blowing system 65 may be located above the substrate 41 and gas may be blown against the surface of the sample via the through-hole 42.

(2) Operation

Since gas can be blown directly against the sample, measurements can be made while gas is adsorbed evenly on the surface of the sample. The invention is useful for analysis of new materials (such as zeolite and porous metal complexes) that are expected as materials occluding methane or hydrogen.

The present invention can be widely applied to solid-state NMR spectroscopy. In the past, a sample in the form of a thin film has been peeled off and pulverized or broken up into small pieces and loaded into a conventional cylindrical rotor prior to measurements. Therefore, there has been the problem that a sample in thin-film form cannot be measured. Another problem has been that the sensitivity is low because the amount of sample is small.

In contrast, in the present invention, a relatively large amount of sample can be used by mounting a holder for a thin-film sample to the front end of a rotor. Furthermore, high-sensitivity measurements are enabled without modifying the thin-film state. In addition, the sample is held at one end of the rotor perpendicularly to the axis of spinning and so, during measurements, the sample can be irradiated with laser light or various waves such as microwaves or terahertz waves or various gases can be blown against the sample. This permits in-situ measurements of various reactions causing structural variations or deterioration of a thin film. Thus, it can be said that the present invention involves a great inventive step.

Effects produced by the present invention can be classified into three categories: fundamental effects, applied effects, and industrial effects which are separately discussed below.

(1) Fundamental Effects: A single thin film of sample can be measured at high sensitivity and high resolution.

In one case, one thin film of sample having a thickness of 2 µm and a diameter of 2.4 mm was loaded into a rotor of 4 mm without peeling off the film from its supporting basic material and measured with a conventional instrument. In a second case, a thin film of sample having a thickness of 2 µm and a diameter of 7 mm was measured in accordance with the present invention.

The S/N of NMR cannot be discussed straightforwardly because coil shape, sample volume, Q value of the NMR probe, filling factor, and other factors complexly contribute to the S/N. However, the related art instrument and the inventive instrument are not greatly different in filling factor and Q value of NMR probe. Therefore, it is considered that the volume of the sample contributes greatly to the S/N.

For this reason, as a rough estimate, the same 8.5 times increase in S/N as the sample volume ratio is estimated. In this case, the time taken to obtain an NMR signal is reduced to $1/(8.5)^2=1/72$. In the present prototype, the diameter of the thin-film sample was 7 mm. A sample holder having a diameter of 12 mm was successfully spun. In this case, a 25 times increase in S/N is estimated. The experiment time can be shortened to 1/625. This means that the duration of an experiment can be shortened from 26 days to 1 hour.

The amount of a sample in thin film form is intrinsically quite small. Therefore, it is quite difficult to perform solid-state NMR measurements of thin-film samples. Almost no experiments were made. We have succeeded in performing $^{27}$Al MAS NMR measurements of thin film of metal aluminum having a thickness of 2 µm owing to the present invention. Our experimental data have shown that it takes a quite long time at present to observe a thin-film sample having a thickness on the nanometer order and, therefore, it is difficult to achieve such an observation. The system currently fabricated is not yet optimized in terms of sensitivity and resolution. Therefore, it is considered that there is plenty of room for improvement.

Figure 16A:
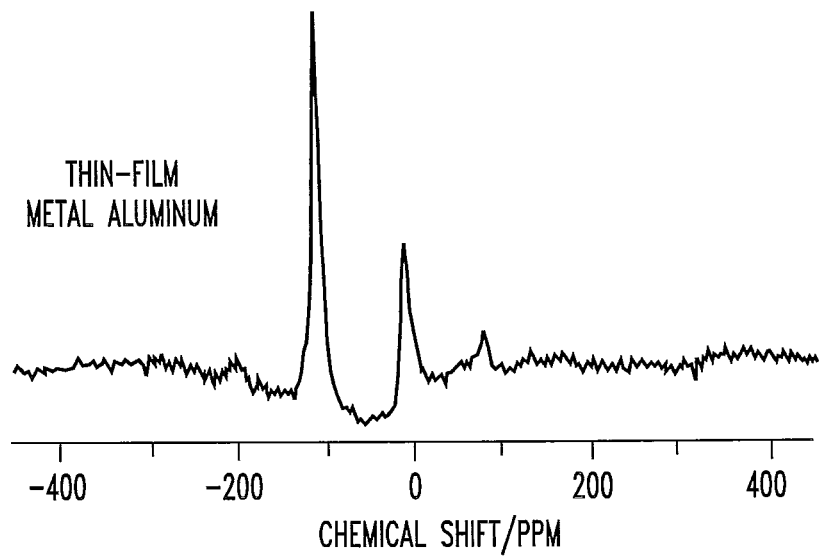
FIG. 16 shows NMR spectra of samples actually obtained by a solid-state NMR spectrometer associated with the invention.
Figure 16B:
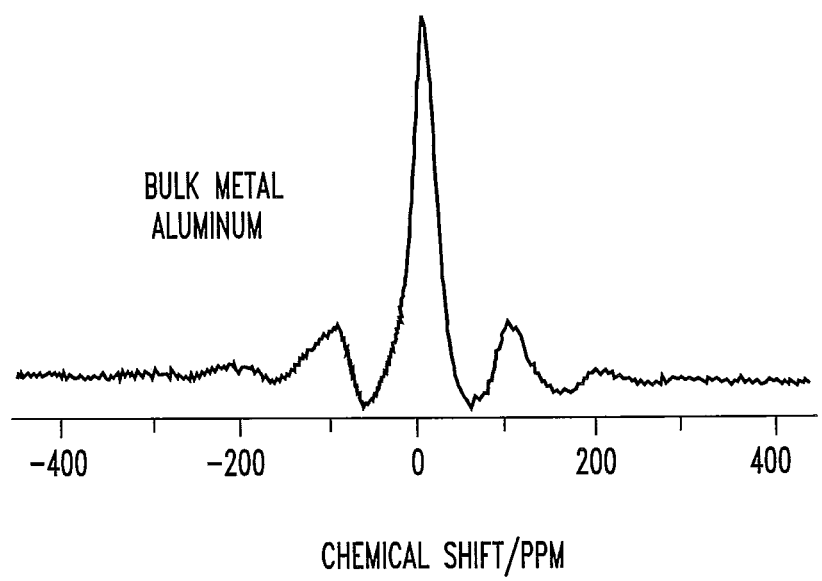

Furthermore, shaping a sample into a thin film provides unique structural information, which is quite interesting scientifically and industrially. FIG. 16A shows a high-resolution solid-state NMR spectrum of a thin-film sample of metal aluminum derived by the experimental prototype instrument. FIG. 16B shows a high-resolution solid-state NMR spectrum of a bulk sample obtained by a conventional instrument.

FIG. 16A shows the $^{27}$Al MAS NMR spectrum of the metal aluminum in the form of a thin film having a thickness of 2 µm. The measurement was made at a spinning rate of 7.4 kHz, a carrier frequency of 78 MHz, an accumulation time of about 12 hours, and a probe Q value of 70. FIG. 16B shows the result of a measurement performed on a sample in the form of a bulk metal aluminum with which KBr was mixed to smoothen spinning of the sample.

In these two spectra, $^{27}$Al nucleus of metal aluminum is observed but it is obvious that they are different in spectral sideband pattern. This shows that shaping a sample into a thin film form has caused the variation.

As shown in this experimental example, the present invention provides an epoch-making technique of obtaining unique molecular structure information arising from thin-film form by accomplishing a completely nondestructive, in-situ, high-resolution NMR spectroscopy of a thin-film sample. This permits an analytical evaluation of the sample, assures the quality, and gives guidance in development. It is considered that the invention has a quite great impact on the industry where thin films are treated.

(2) Applied Effects: An external field can be applied by spatially separating a rotating mechanism and a measuring mechanism from each other.

The advantage of the shape of the surface coil is that laser light can be directed from a direction normal to the surface of the thin film through the central space. By utilizing this advantage, an external field that varies a physical property of the thin film such as light, microwaves, electric field, gas, or heat source of laser light can be efficiently applied to the sample.

A case in which laser heating is done is now discussed. With a normal NMR probe, there is a sample spinning module made of plastic around the sample and so it can be heated up to about 150° C. When a special probe made of zirconia for high-temperature MAS (see U.S. Pat. No. 5,202,633) is used, MAS experiments can be performed at 650° C. or higher.

On the other hand, in the present invention, there is no sample spinning module around the sample and so it is easy to heat the sample. When the sample is locally heated using laser heating, the whole sample can be heated to 1000° C. instantly.

There is a technique, known as photoinduced triple-dynamic nuclear polarization, that increases the NMR sensitivity by a factor of tens of thousands by irradiating a sample with microwaves and laser light (K. Takeda, et al., J. Phys. Soc. Jpn., vol. 73, pp. 2313-2318). In the present invention, the sample is thin and, therefore, the sample is efficiently irradiated with laser light. Consequently, it is expected that polarization experiments will be performed efficiently.

High-resolution solid-state NMR spectroscopy can be performed by spinning the sample at high speed while exerting such an external action on the sample. Furthermore, by contriving the shape of the sample holder, high-resolution solid-state NMR spectroscopy of powdered sample under an external action is possible, as well as of a thin-film sample.

(3) Industrial Effects: Applications to the Industry (field, finished products, instrument, method, and so on)

Today, advanced functional thin-film devices such as thin-film lithium ion cells, thin-film solar cells, and organic electroluminescent devices are under active development. A thin-film device is made of a thin-film material formed by stacking layers of atoms or molecules on a substrate. The thin-film material is a composite including a substrate. If only the thin-film portion is taken out, the intentional function will not be fulfilled. In order to measure the function, it is essential that the sample be in its intrinsic state, i.e., a thin film on a substrate. Therefore, in order to develop a device, there is a strong need for understanding of the relation between a thin-film material in the state of final device and the function of the device.

In evaluating the structure of a thin-film sample, an electron beam or X-rays are used. Because of short wavelength, there is high spatial resolution but the penetration distance is short. Therefore, it is necessary that the sample be processed or measured in a vacuum. There is the possibility that processing the sample will vary the state of the sample or the sample will evaporate under a vacuum. Furthermore, light elements having small scattering cross sections and amorphous substances having no periodic structure are unsuited for measurements.

NMR spectroscopy offers quite useful information from the atomic or molecular level if the sample is an amorphous material or made of a light element that is difficult to measure with an electron beam or X-rays. Furthermore, radio waves of lower frequencies are used unlike electron beam and X-rays. Therefore, almost all thin-film materials are transparent except for the case where the waves do not penetrate because of a superconducting state. The sample can be measured without destroying it while the sample is in a device state.

In the related art, many thin-film samples need to be fabricated expressly in conformity with the inside diameter of the sample tube for measurements. In the case of a single large thin-film sample, it is necessary that the sample be peeled off or the whole sample including the substrate be pulverized and loaded into a sample tube. This leads to a cost increase or impairs the merit of NMR, i.e., nondestructive measurements. When one sample is prepared in conformity with the inside diameter of a sample tube, the filling factor is poor and so the sensitivity is low. This makes a measurement unfeasible or, if possible, a quite long time is required.

The present invention achieves over 10 times higher sensitivity even if the sample is a single thin film. This means that the measurement time is reduced to one-hundredth. This improves the throughput. In addition, multidimensional NMR spectroscopy which would have been heretofore difficult to perform but which offers a larger amount of information is enabled. Consequently, leading-edge thin-film devices can be measured nondestructively.

One example of the leading-edge thin-film devices is a thin-film lithium ion cell. Although in a test stage in 2005, the market of thin-film lithium ion batteries are forecasted to reach 10 billion units and 11 billion U.S. dollars in 2012 ("Nanotechnology and Thin Film Lithium and Lithium Ion Battery Market Opportunities, Strategies, and Forecasts, 2006 to 2012", WinterGreen Research, Inc.). There is a strong demand for an evaluation technique to achieve further improved characteristics.

A secondary battery deteriorates as it is repeatedly charged and discharged but its mechanism is not understood. In the related art solid-state NMR spectroscopy, in a case where a battery is charged and discharged and a measurement is made, it is carried out at low resolution without spinning. To make high-resolution measurements, it is customary that the cell is destroyed and the constituent elements are taken out. However, it is considered that the mechanism of impairing the cell arises from local structures or phase variations. To analyze them quantitatively, high-resolution measurements are necessary. If the cell is destroyed, further charging and discharging cycles can no longer be performed. Accordingly, in order to trace deterioration that is a hysteresis phenomenon, nondestructive measurements are required.

The present invention makes it possible to measure a thin-film lithium ion battery at high resolution while the battery is in a device form. Therefore, a new means can be offered which traces deterioration of the battery quantitatively on an atomic level by repeating a cycle consisting of charging and discharging the battery and making a high-resolution measurement.

Amorphous silicon solar cells and organic electroluminescent devices are functional thin-film devices which have been already marketed. There is a demand for knowledge about the correlation between the thin-film material and the function of the battery in device form for both types of devices. It is considered that the present invention caters for the requirement.

Furthermore, the sample can be easily acted on variously from the outside by spatially separating the rotating portion and the sample portion from each other. Therefore, measurements can be made under an environment where the device operates in practice. In the case of laser heating, a structure containing a defect can be analyzed by performing high-resolution solid-state NMR spectroscopy of an oxide electrolyte used in a solid oxide fuel cell (SOFC) that is the most efficient fuel cell at the operating temperature of the SOFC, i.e., 1,000° C.

In a solid electrolyte, the structure of defects is directly associated with ion conductivity that is a physical property, and is quite important information because it gives guidance on developing and designing materials. High-resolution solid-state NMR spectroscopy is an almost only one means capable of analyzing defect structures and can be applied in environment and energy fields such as batteries, gas sensors, and permselective membranes.

What is claimed is:

1. A solid-state NMR spectrometer for obtaining a solid-state NMR spectrum by directing RE excitation pulses to a sample from a transmit coil while spinning a rotor at high speed about an axis tilted at a magic angle of about 54.7° to a static magnetic field, said spectrometer comprising:
   a rotor having a concave bore;
   a disklike sample-holding portion permitting a sample to be placed on its surface or received in an internal cavity formed in the sample-holding portion and a convex pillar portion mounted on a central portion of a rear surface of the disklike sample-holding portion, and wherein the sample-holding portion is mounted to an end portion of the rotor by the convex pillar portion inserted in the concave bore of the rotor;
   a stator having an air bearing placed within the static magnetic field, the rotor being disposed in the stator; and
   an engaging mechanism detachably holding said sample-holding portion.

2. The solid-state NMR spectrometer of claim 1, wherein said transmit coil is held by a disk-shaped transmit coil holder which is designed to be capable of adjusting the distance between the transmit coil and a sample held on the disklike sample holding portion.

3. The solid-state NMR spectrometer of claim 2, wherein said transmit coil holder is provided with an opening in a position corresponding to a central portion of the transmit coil to permit at least one type of light, microwaves, electric field, gas, and heating laser light which vary a physical property of the sample to act on the sample.

4. The solid-state NMR spectrometer of claim 1, wherein said transmit coil is substantially identical in diameter to said disklike sample-holding portion.

5. The solid-state NMR spectrometer of claim 1, wherein said disklike sample-holding portion is spun at high speed on a plane tilted at about 35.3° to the static magnetic field.

6. The solid-state NMR spectrometer of claim 1, wherein said sample is a thin-film sample and placed on the surface of said disklike sample-holding portion.

7. The solid-state NMR spectrometer of claim 1, wherein the sample is a powdered sample and loaded in the internal cavity of said disklike sample-holding portion.

8. A sample holder for use in the solid-state NMR spectrometer of claim 1, said sample holder comprising:

a disklike sample-holding portion permitting the sample to be placed on its surface or received in an internal cavity formed in the sample holding portion; and a pillar portion mounted in a central portion of a rear surface of the disklike sample-holding portion;

wherein the sample holder is mounted to the one-end portion of the rotor by said engaging mechanism via the pillar portion.

9. A method of solid-state NMR spectroscopy for obtaining a solid-state NMR spectrum by the use of the solid-state NMR spectrometer of claim 1.

10. The method of solid-state NMR spectroscopy of claim 9, wherein when the solid-state NMR spectrum is obtained, the sample held on or in the sample holder is acted on by at least one type of laser light, microwaves, heat rays, hot air, cold air, and electric power supplied via a wireless power feeding coil.

* * * * *